US011260160B2

(12) United States Patent
Matsubara et al.

(10) Patent No.: US 11,260,160 B2
(45) Date of Patent: Mar. 1, 2022

(54) SYSTEMS AND METHODS FOR IMPROVING AN AV ACCESS SITE

(71) Applicant: VOLCANO CORPORATION, San Diego, CA (US)

(72) Inventors: Bradley S. Matsubara, Escondido, CA (US); John Unser, Temecula, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 74 days.

(21) Appl. No.: 14/596,785

(22) Filed: Jan. 14, 2015

(65) Prior Publication Data

US 2015/0297818 A1     Oct. 22, 2015

Related U.S. Application Data

(60) Provisional application No. 61/927,056, filed on Jan. 14, 2014.

(51) Int. Cl.
*A61B 8/00*    (2006.01)
*A61M 1/36*    (2006.01)
(Continued)

(52) U.S. Cl.
CPC ........... *A61M 1/3655* (2013.01); *A61B 5/026* (2013.01); *A61B 5/02154* (2013.01); *A61B 8/12* (2013.01);
(Continued)

(58) Field of Classification Search
CPC .......... A61B 17/12009; A61B 2505/05; A61B 5/02154; A61B 5/026; A61B 8/06;
(Continued)

(56) References Cited

U.S. PATENT DOCUMENTS 4,733,669 A * 3/1988 Segal .................. A61B 5/6886
600/465
4,794,931 A    1/1989 Yock
(Continued)

FOREIGN PATENT DOCUMENTS

CA    2 616 760 A1    2/2007
EP    1 820 436 A2    8/2007
(Continued)

OTHER PUBLICATIONS

Orford et al, Routine intravascular ultrasound guidance of percutaneous coronary intervention, J Am Coll Cardiol. 2004;43(8):1335-1342.*

(Continued)

*Primary Examiner* — Christopher L Cook (57) ABSTRACT

The invention relates to restricting flow through a vascular access site such as an arteriovenous (AV) fistula or a graft using intravascular measurements to guide the procedure. The invention provides systems and methods for using intravascular detection to guide the restriction of flow through an AV fistula or graft. An intravascular instrument such as an imaging catheter or guidewire with measuring capabilities is inserted into a vessel proximal to an access site and used to evaluate the access site, which is banded to obtain healthy flow as indicated by the intravascular instrument. In certain aspects, the invention provides a method for improving a hemodialysis fistula or graft by inserting an intravascular instrument into a vessel proximal to the fistula or graft, making a measurement with the intravascular instrument, and restricting flow through the fistula or graft until the measurement obtains a predetermined value.

18 Claims, 6 Drawing Sheets

(51) Int. Cl.
  *A61B 8/12* (2006.01)
  *A61B 5/0215* (2006.01)
  *A61B 5/026* (2006.01)
  *A61B 17/12* (2006.01)
  *A61B 34/00* (2016.01)
  *A61B 90/00* (2016.01)
  *A61B 8/06* (2006.01)

(52) U.S. Cl.
  CPC ........... *A61B 8/06* (2013.01); *A61B 17/12009* (2013.01); *A61B 34/25* (2016.02); *A61B 2090/3966* (2016.02); *A61B 2505/05* (2013.01); *A61M 2205/3303* (2013.01); *A61M 2205/3331* (2013.01)

(58) Field of Classification Search
  CPC ... A61B 2090/3966; A61B 34/25; A61B 8/12; A61M 1/3655; A61M 2205/3303; A61M 2205/3331
  See application file for complete search history.

(56) References Cited

U.S. PATENT DOCUMENTS

| | | |
|---|---|---|
| 4,841,977 A | 6/1989 | Griffith et al. |
| 4,917,097 A | 4/1990 | Proudian et al. |
| 4,951,677 A | 8/1990 | Crowley et al. |
| 5,000,185 A | 3/1991 | Yock |
| 5,095,911 A | 3/1992 | Pomeranz |
| 5,125,137 A | 6/1992 | Corl et al. |
| 5,135,486 A | 8/1992 | Eberle et al. |
| 5,163,445 A | 11/1992 | Christian et al. |
| 5,167,233 A | 12/1992 | Eberle et al. |
| 5,174,295 A | 12/1992 | Christian et al. |
| 5,176,141 A | 1/1993 | Bom et al. |
| 5,178,159 A | 1/1993 | Christian |
| 5,183,048 A | 2/1993 | Eberle |
| 5,226,421 A | 7/1993 | Frisbie et al. |
| 5,240,003 A | 8/1993 | Lancee et al. |
| 5,240,437 A | 8/1993 | Christian |
| 5,243,988 A | 9/1993 | Sieben et al. |
| 5,313,949 A | 5/1994 | Yock |
| 5,321,501 A | 6/1994 | Swanson et al. |
| 5,326,342 A | 7/1994 | Pflueger et al. |
| 5,348,017 A | 9/1994 | Thornton et al. |
| 5,353,798 A | 10/1994 | Sieben |
| 5,368,037 A | 11/1994 | Eberle et al. |
| 5,372,138 A | 12/1994 | Crowley et al. |
| 5,373,845 A | 12/1994 | Gardineer et al. |
| 5,373,849 A | 12/1994 | Maroney et al. |
| 5,375,602 A | 12/1994 | Lancee et al. |
| 5,453,575 A | 9/1995 | O'Donnell et al. |
| 5,771,895 A | 6/1998 | Slager |
| 5,830,222 A | 11/1998 | Makower |
| 5,873,835 A | 2/1999 | Hastings et al. |
| 6,068,638 A | 5/2000 | Makower |
| 6,106,476 A * | 8/2000 | Corl ..................... A61B 5/0215 600/486 |
| 6,134,003 A | 10/2000 | Tearney et al. |
| 6,159,225 A | 12/2000 | Makower |
| 6,190,353 B1 | 2/2001 | Makower et al. |
| 6,200,268 B1 | 3/2001 | Vince et al. |
| 6,210,339 B1 | 4/2001 | Kiepen et al. |
| 6,283,951 B1 | 9/2001 | Flaherty et al. |
| 6,375,615 B1 | 4/2002 | Flaherty et al. |
| 6,381,350 B1 | 4/2002 | Klingensmith et al. |
| 6,421,164 B2 | 7/2002 | Tearney et al. |
| 6,457,365 B1 | 10/2002 | Stephens et al. |
| 6,508,824 B1 | 1/2003 | Flaherty et al. |
| 6,544,230 B1 | 4/2003 | Flaherty et al. |
| 6,551,250 B2 | 4/2003 | Khalil |
| 6,579,311 B1 | 6/2003 | Makower |
| 6,602,241 B2 | 8/2003 | Makower et al. |
| 6,655,386 B1 | 12/2003 | Makower et al. |
| 6,659,957 B1 | 12/2003 | Vardi et al. |
| 6,660,024 B1 | 12/2003 | Flaherty et al. |
| 6,669,709 B1 | 12/2003 | Cohn et al. |
| 6,685,648 B2 | 2/2004 | Flaherty et al. |
| 6,709,444 B1 | 3/2004 | Makower |
| 6,726,677 B1 | 4/2004 | Flaherty et al. |
| 6,746,464 B1 | 6/2004 | Makower |
| 6,780,157 B2 | 8/2004 | Stephens et al. |
| 7,074,188 B2 | 7/2006 | Nair et al. |
| 7,175,597 B2 | 2/2007 | Vince et al. |
| 7,215,802 B2 | 5/2007 | Klingensmith et al. |
| 7,245,789 B2 | 7/2007 | Bates et al. |
| 7,359,554 B2 | 4/2008 | Klingensmith et al. |
| 7,387,636 B2 | 6/2008 | Cohn et al. |
| 7,447,388 B2 | 11/2008 | Bates et al. |
| 7,463,759 B2 | 12/2008 | Klingensmith et al. |
| 7,527,594 B2 | 5/2009 | Vardi et al. |
| 7,660,492 B2 | 2/2010 | Bates et al. |
| 7,736,317 B2 | 6/2010 | Stephens et al. |
| 7,783,337 B2 | 8/2010 | Feldman et al. |
| 7,787,127 B2 | 8/2010 | Galle et al. |
| 7,995,210 B2 | 8/2011 | Tearney et al. |
| 7,999,938 B2 | 8/2011 | Wang |
| 8,059,923 B2 | 11/2011 | Bates et al. |
| 8,108,030 B2 | 1/2012 | Castella et al. |
| 8,486,062 B2 | 7/2013 | Belhe et al. |
| 8,486,063 B2 | 7/2013 | Werneth et al. |
| 2002/0010487 A1 | 1/2002 | Evans et al. |
| 2002/0183632 A1 * | 12/2002 | Krivitski ............. A61M 1/3656 600/505 |
| 2004/0146546 A1 | 7/2004 | Gravett et al. |
| 2005/0196026 A1 | 9/2005 | Klingensmith et al. |
| 2005/0249391 A1 | 11/2005 | Kimmel et al. |
| 2006/0064159 A1 * | 3/2006 | Porter ................... A61B 17/11 623/1.24 |
| 2006/0241342 A1 | 10/2006 | Macaulay et al. |
| 2006/0241505 A1 * | 10/2006 | Ahmed ............. A61B 5/02158 600/486 |
| 2007/0016034 A1 | 1/2007 | Donaldson |
| 2007/0066890 A1 * | 3/2007 | Maschke ............. A61B 5/0066 600/424 |
| 2007/0232933 A1 | 10/2007 | Gille et al. |
| 2008/0097497 A1 * | 4/2008 | Assad ................... A61B 17/12 606/157 |
| 2008/0119739 A1 | 5/2008 | Vardi et al. |
| 2008/0171944 A1 | 7/2008 | Brenneman et al. |
| 2008/0180683 A1 | 7/2008 | Kemp |
| 2008/0291463 A1 | 11/2008 | Milner et al. |
| 2009/0018393 A1 | 1/2009 | Dick et al. |
| 2009/0024085 A1 | 1/2009 | To et al. |
| 2009/0043191 A1 | 2/2009 | Castella et al. |
| 2009/0088650 A1 | 4/2009 | Corl |
| 2009/0195514 A1 | 8/2009 | Glynn et al. |
| 2009/0284332 A1 | 11/2009 | Moore et al. |
| 2010/0087732 A1 | 4/2010 | Eberle et al. |
| 2010/0130864 A1 | 5/2010 | Donnelly et al. |
| 2010/0220334 A1 | 9/2010 | Condit et al. |
| 2011/0060229 A1 | 3/2011 | Hulvershorn et al. |
| 2011/0152771 A1 | 6/2011 | Milner et al. |
| 2011/0306995 A1 | 12/2011 | Moberg |
| 2011/0319752 A1 | 12/2011 | Steinberg et al. |
| 2012/0108943 A1 | 5/2012 | Bates et al. |
| 2012/0230565 A1 | 9/2012 | Steinberg et al. |
| 2013/0030295 A1 | 1/2013 | Huennekens et al. |
| 2013/0030303 A1 | 1/2013 | Ahmed et al. |
| 2013/0046167 A1 | 2/2013 | Shah |
| 2013/0137980 A1 | 5/2013 | Waters et al. |
| 2013/0296704 A1 | 11/2013 | Magnin et al. |
| 2013/0303907 A1 | 11/2013 | Corl |

FOREIGN PATENT DOCUMENTS

| | | |
|---|---|---|
| WO | 91/17710 A1 | 11/1991 |
| WO | 03/030744 A1 | 4/2003 |
| WO | 2014/100226 A1 | 6/2014 |
| WO | 2014/109879 A1 | 7/2014 |
| WO | 2014/143816 A1 | 9/2014 |
| WO | 2014/150401 A1 | 9/2014 |

(56) References Cited

FOREIGN PATENT DOCUMENTS

OTHER PUBLICATIONS

Higuchi et al., "Intravascular ultrasound imaging before and after angioplasty for stenosis of arteriovenous fistulae in haemodialysis patients", Nephrology Dialysis Transplantation, 2001.*
Anonymous, 2006, Clinical Practice Guidelines and Clinical Practice Recommendations 2006 Updates, National Kidney Foundation:10PP.
International Search Report and Written Opinion dated May 4, 2015, for International Patent Application No. PCT/US2015/011337, filed Jan. 14, 2015 (16 pages).
International Search Report and Written Opinion dated Apr. 28, 2015, for International Patent Application No. PCT/US2015/011357, filed Jan. 14, 2015 (11 pages).
International Search Report and Written Opinion dated Apr. 10, 2015, for International Patent Application No. PCT/US2015/011397, filed Jan. 14, 2015 (14 pages).
International Search Report and Written Opinion dated Apr. 21, 2015, for International Patent Application No. PCT/US2015/011359, filed Jan. 14, 2015 (10 pages).
International Search Report and Written Opinion dated Apr. 28, 2015, for International Patent Application No. PCT/US2015/011411, filed Jan. 14, 2015 (11 pages).
Toregeani et al., Evaluation of hemodialysis arteriovenous fistula maturation by color-flow Doppler ultrasound, J Vasc Bras 7(3):203-2013, 2008.
Ferring, et al., Vascular ultrasound for the pre-operative evaluation prior to arteriovenous fistula formation for haemodialysis: review of the evidence, Nephrol. Dial. Transplant. 23(6):1809-1815, 2008.
Robbin, et al., Hemodialysis arteriovenous fistula maturity: US evaluation, Radiology 225(1):59-64, 2002.
Harrison et al., What's in a name?, J Endo Ther 14(6):797-801, 2011.
West et al., Arterial insufficiency in hemodialysis access procedures: correction by banding technique, Transpl Proc 23(2): 1838-40, 1991.
Rivers, et al., 1992, Correction of steal syndrome secondary to hemodialysis access fistulas: a simplified quantitative technique, Surgery 112(3):593-7.
Kirkman, 1991, Technique for flow reduction in dialysis access fistulas, Surg Gyn Obstet 172(3):231-3.
Mickley, 2008, Steal Syndrome—strategies to preserve vascular access and extremity, Nephrol Dial Transplant 23:19-24.
Miller et al., 2006, Minimally Invasive Limited Ligation Endoluminal-assisted Revision (MILLER) for treatment of dialysis access-associated steal syndrome, Kidney Int 70(4):765-70.
Schneider, et al., 2006, T-banding: A technique for flow reduction of a hyper-functioning arteriovenous fistula, J Vasc Surg.
Miller, et al., 2009, The MILLER banding procedure is an effective method for treating dialysis-associated steal syndrome, Kidney Int 1-8.
Wang et al., "Optimizing the Beam Pattern of a Forward-Viewing Ring-Annular Ultrasound Array for Intravascular Imaging", Transactions on Ultrasonics, Ferroelectrics, and Frequency Control, vol. 49, No. 12, Dec. 2002.
Fleming et al., "Real-time monitoring of cardiac radio-frequency ablation lesion formation using an optical coherence tomography forward-imaging catheter.," J. Biomed. Opt. 15, (3 ), 030516-030513 (2010).
Wang et al. "In vivo intracardiac optical coherence tomography imaging through percutaneous access: toward image-guided radio-frequency ablation". J. Biomed. Opt. 0001;16(11):110505-110505-3. doi:10.1117/1.3656966.
Seward et al., Mayo Clinic Proceedings 71(7):629-635 (1996).
Bail et al.; 'Optical coherence tomography with the "Spectral Radar"—Fast optical analysis in volume scatterers by short coherence interferometry' Optics letters vol. 21, No. 14 (1996) 1087-1089.
Smith et al., 'Absolute displacement measurements using modulation of the spectrum of white light in a Michelson interferometer' Applied Optics, vol. 28, No. 15, 1989, 3339-3342.

* cited by examiner

FIG. 6

SYSTEMS AND METHODS FOR IMPROVING AN AV ACCESS SITE

RELATED APPLICATIONS

The present application claims the benefit of and priority to U.S. provisional application Ser. No. 61/927,056, filed Jan. 14, 2014, the content of which is incorporated by reference herein in its entirety.

FIELD OF THE INVENTION

The invention relates to restricting flow through arteriovenous fistulas or grafts using intravascular measurements to guide the procedure.

BACKGROUND

Healthy kidneys remove waste and minerals from the blood. When kidneys fail, harmful waste builds up in the body, blood pressure may rise, and the body may retain excess fluid and not make enough red blood cells due to insufficient erythropoietin production. Hemodialysis is a common method for treating kidney failures and involves flowing blood through a filter to remove wastes. For hemodialysis, an arteriovenous (AV) fistula is created that connects an artery to a vein, or optionally an AV graft is created by using a tube to connect the artery to the vein. Organizations such as the National Kidney Foundation generally agree that fistulas are the best type of vascular access. A fistula is deemed to be ready for use, or mature, once adequate blood flows through it. However, too much blood flow can cause serious adverse consequences. For example, a high flow fistula can lead to hemodialysis access-induced distal ischemia, cardiac overload, or both.

Distal ischemia is associated with a lack of blood flow to the extremities and is characterized by symptoms of ischemia, and in extreme cases, tissue death. High flow through the fistula can also compromise cardiac function, causing cardiomegaly.

SUMMARY

The invention provides methods of using intravascular detection to guide the restriction of flow through a vascular access site such as an AV fistula or graft so that flow is maintained at a desired and healthy level. An intravascular guidewire or catheter with measuring capabilities is inserted into a vessel proximal to a fistula or graft and used to evaluate the fistula. For example, an IVUS catheter can be used to image the fistula/graft or a functional management guidewire can be used to measure flow. An operator can determine a target flow volume, assess flow through the fistula or graft, and performing a restriction operation (e.g., banding). The resultant flow is assessed and used to guide the restriction operation until the target flow volume is obtained. Intravascular evaluation can include imaging to determine fistula patency (e.g., interior diameter), pressure sensing (i.e., to determine a AP across the fistula), Doppler flow velocity, others, or a combination thereof. Those intravascular measures can be used to guide banding. This results in an AV fistula or graft that provides good access for hemodialysis. Due to the banding, the fistula or graft will not exhibit the excessive flow associated with cardiomegaly or distal ischemia. Thus more patients can experience successful hemodialysis and have an improved quality of life despite kidney problems.

Devices and methods of the invention can be used to guide restriction for any vascular access site, including arteriovenous (AV) fistulas and grafts. An AV fistula is a surgically-created or induced native channel formed to connect an artery to a vein, whereas an AV graft is an artificial connection (such as a synthetic material) that connects the artery to the vein.

In certain aspects, the invention provides a method for improving a hemodialysis vascular access site such as an AV fistula or a graft by inserting an intravascular instrument into a vessel proximal to the vascular access site, making a measurement with the intravascular instrument, and restricting flow through the vascular access site until the measurement obtains a predetermined value. The intravascular instrument may include an ultrasound catheter or an instrumented guidewire. A computer may be used to evaluate whether the predetermined value is obtained and guide a decision about further restriction of flow. The measurement may be a rate of flow through the fistula (and the predetermined value may be, e.g., less than 800 mL/min). The measurement may be a radius or diameter of the fistula or graft (and the predetermined value may be, e.g., less than an 8 mm diameter).

In some embodiments, the measurement is taken continually during the step of restricting the flow. Preferably, flow is restricted by a banding procedure.

In related aspects, the invention provides a system for AV fistula or graft banding. The system includes an intravascular instrument dimensioned to be inserted into a vessel proximal to an arteriovenous fistula or graft and operable to measure a property therein and a computer coupled to the intravascular instrument and operable to receive the measured property and evaluate a need for restriction of blood flow through the arteriovenous fistula or graft. The computer includes a processor coupled to a non-transitory memory having stored therein instructions executable to cause the system to evaluate whether the measured property obtains a predetermined value and guide a decision about further restriction of flow. A "standard", or predetermined value, is preferably also stored in the memory. In some embodiments, the intravascular instrument is an ultrasound catheter. The measured property may include a radius or diameter of the fistula or graft. The predetermined diameter value may be less than 8 mm.

In certain embodiments, the intravascular instrument is an instrumented guidewire. The measured property may include a rate of flow through the fistula (e.g., as measured by Doppler flow velocity using, for example, forward-looking IVUS or standard IVUS). Flow volume can be calculated by the computer using measured velocity and vessel cross-sectional area (e.g., from an IVUS instrument, from an angiogram, or as input by a physician). The predetermined value for flow volume may be established within the computer as, for example, less than 800 mL/min.

DETAILED DESCRIPTION

Methods of the invention use an intravascular imaging or measurement tool to guide a procedure for restricting flow through an AV fistula or graft. In some embodiments, intravascular imaging such as rotational IVUS is used. In certain embodiments, functional measurements such as Doppler velocity measurements or pressure measurements are used. Flow can be restricted by a suitable procedure such as surgical banding.

Figure 1:
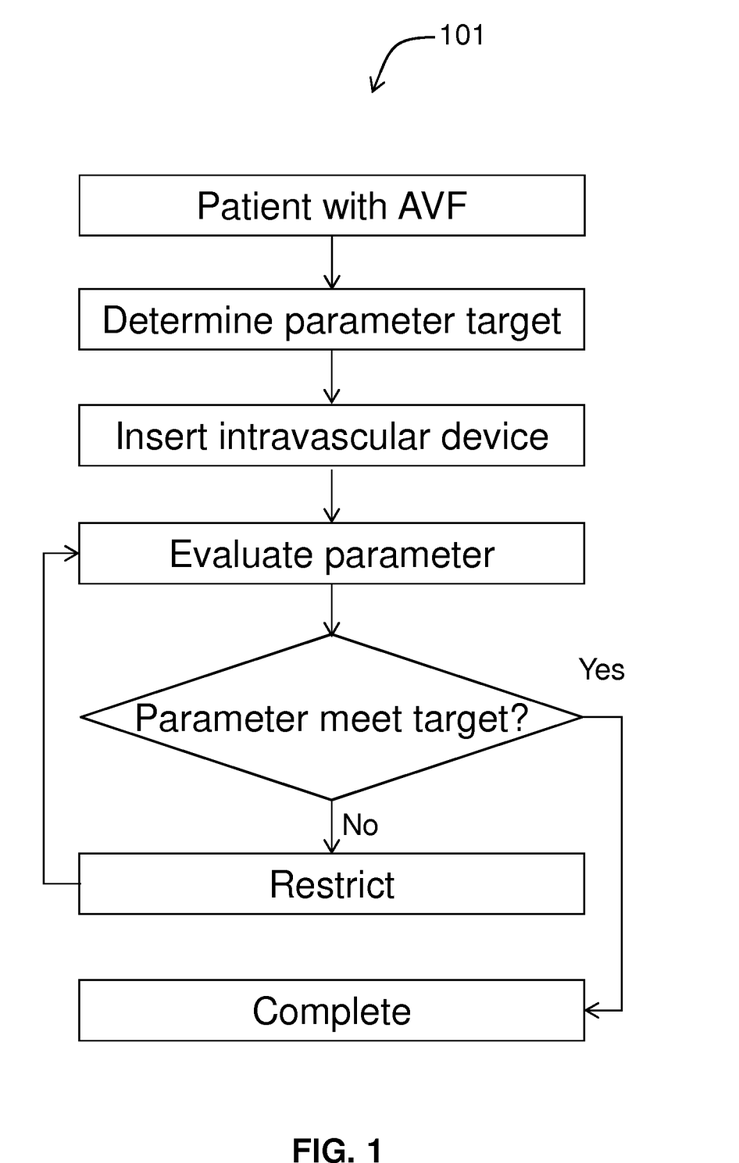
FIG. 1 illustrates a method for intravascular guidance of fistula or graft banding.

FIG. 1 illustrates a method 101 of providing intravascular guidance for fistula banding. Method 101 begins with a patient who has a high-flow AV fistula. One of skill in the art will recognize that a high-flow fistula is associated with flow that is higher than what is best suited to maintain vascular access for hemodialysis. While any suitable criteria can be used for a high-flow fistula, in some embodiments, a flow rate >800 mL/min indicates a need for banding. This is considered in view of a target flow rate—i.e., a flow rate that is well-suited for hemodialysis. An exemplary target flow rate could be 600 mL/min. Existing medical guidelines provide that an adequate fistula has a flow >600 mL/min and a diameter >0.4 cm. A target flow rate is preferably less than about 800 mL/min (e.g., about 600 mL/min).

Methods of the invention include intravascular intervention to evaluate fistula patency or flow and to guide banding. Flow can be evaluated by directly measuring flow rate (e.g., by Doppler velocity) or by measuring pressure or through an intravascular imaging operation to, for example, observe a diameter of the fistula lumen. If the evaluation reveals that that the flow rate exceeds the target, then an operation is performed to restrict flow through the fistula. Any suitable flow restriction operation can be performed. As discussed below, suitable methods for restricting flow include the use of a narrowing suture, plication, minimally invasive limited ligation endoluminal-assisted revision (MILLER) banding, tapering, and surgical banding. Once flow is restricted, it can be evaluated again to determine if the target has been obtained. Once the target is obtained, the procedure is completed. The result is an AV fistula with continued usefulness for hemodialysis. The evaluation of patency or flow can be performed by any intravascular instrument including, for example, an IVUS catheter.

Figure 2:
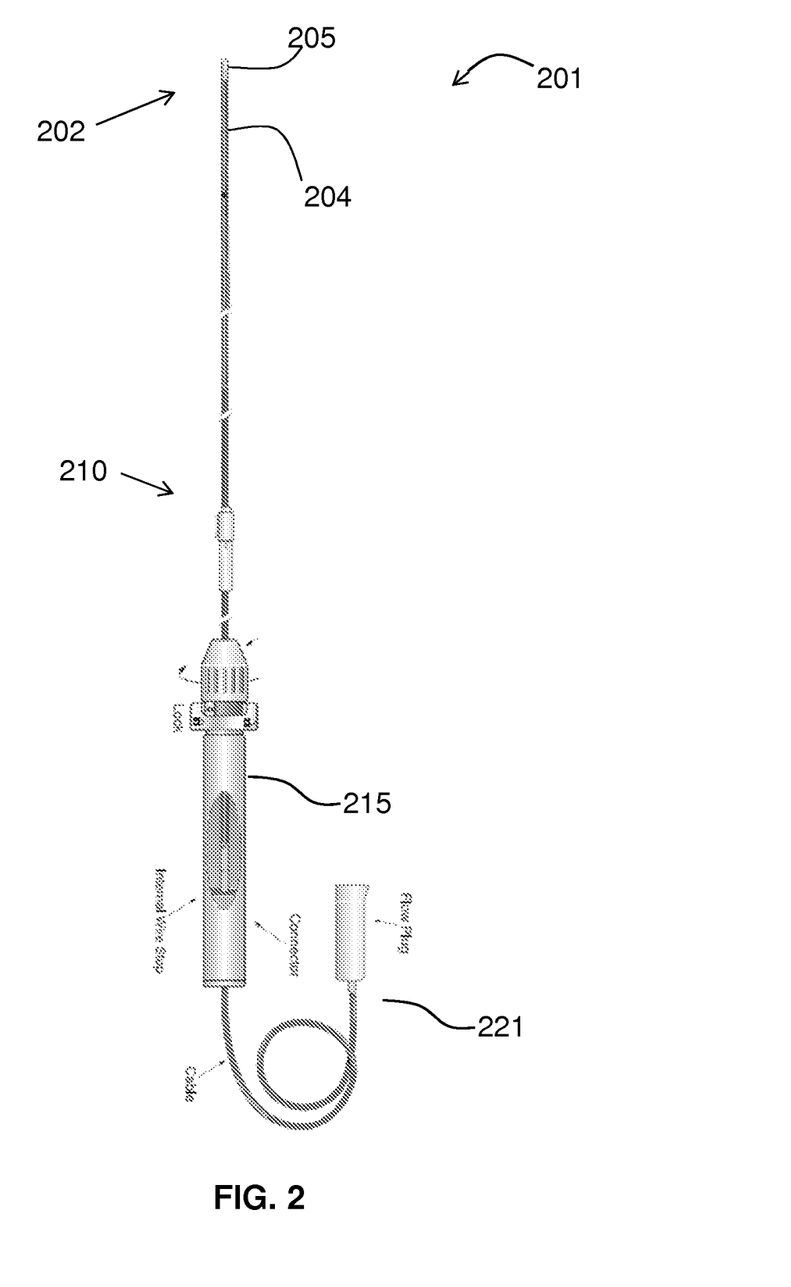
FIG. 2 shows an IVUS catheter to guide fistula or graft banding.

FIG. 2 shows an catheter 201 for rotational intravascular ultrasound (IVUS). IVUS is a catheter based system that allows physicians to acquire images of vessels from within. IVUS provides detailed and accurate measurements of lumen and vessel size, tissue area and volume, and the location of key anatomical landmarks. An IVUS system can include modules for virtual histology so that tissue types can be identified (e.g., plaque, vessel wall, stent, fluid, etc.) within an image. IVUS uses a catheter 201 with an ultrasound probe 205 attached at the distal end 202. The proximal end 210 of the catheter 201 is attached to computerized ultrasound equipment. To visualize a vessel via IVUS, angiographic techniques are used and the physician positions the tip of a guide wire, usually 0.36 mm (0.014") diameter and about 200 cm long. The physician steers the guide wire from outside the body, under angiography guidance and into the blood vessel branch to be imaged.

The ultrasound catheter tip is slid in over the guide wire and positioned, again, using angiography techniques, so that the tip is at the farthest away position to be imaged. Sound waves are emitted from the catheter tip (e.g., in about a 20-40 MHz range) and the catheter also receives and conducts the return echo information out to the external computerized ultrasound equipment, which constructs and displays a real time ultrasound image of a thin section of the blood vessel currently surrounding the catheter tip. Images may be displayed at about 30 frames per second. The guide wire is kept stationary and the tip of catheter 201 is slid backwards, usually under motorized control at a pullback speed of 0.5 mm/s. Systems for IVUS are discussed in U.S. Pat. No. 5,771,895; U.S. Pub. 2009/0284332; U.S. Pub. 2009/0195514 A1; U.S. Pub. 2007/0232933; and U.S. Pub. 2005/0249391, the contents of each of which are hereby incorporated by reference in their entirety. Imaging tissue by IVUS can produce cross-sectional views both down and along a vessel axis. Those views are known as tomographic and ILD views, respectively.

Figure 3:
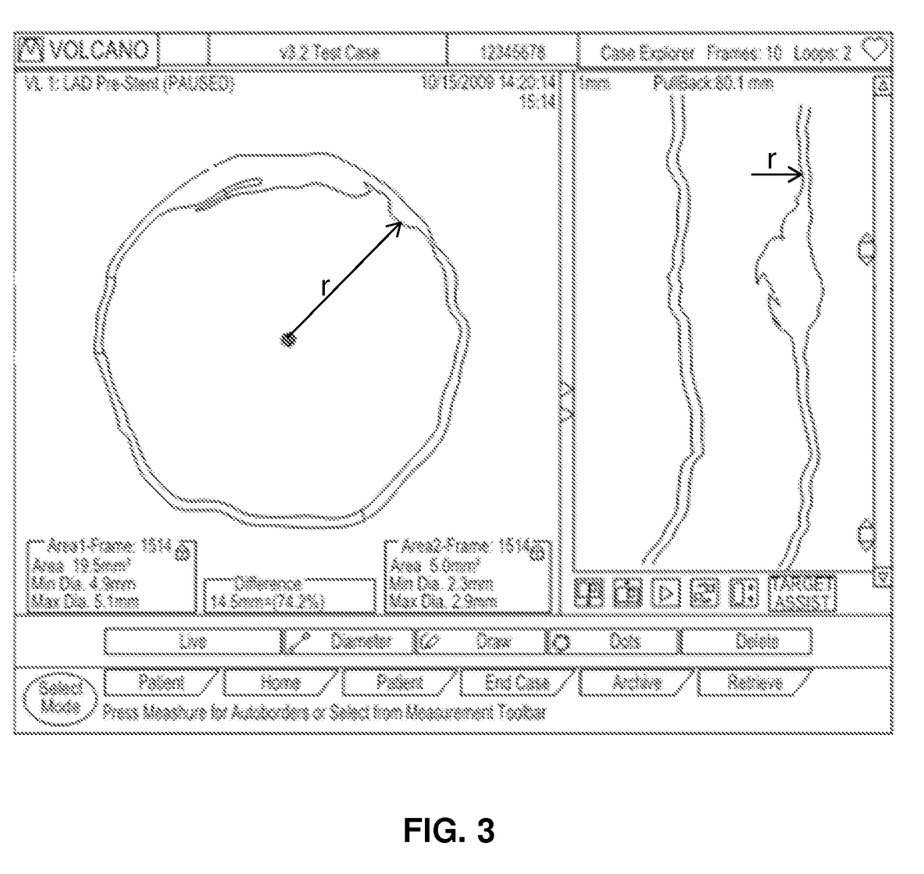
FIG. 3 illustrates a view of a vessel produced by an IVUS catheter.

FIG. 3 illustrates a tomographic view and an ILD view of a vessel produced by IVUS catheter 201. As visual inspection of FIG. 3 illustrates, IVUS can reveal the patency of a vessel. For example, IVUS can reveal, through the tomographic view, the ILD, or both, the radius r (or diameter) of the vessel. IVUS may optionally be performed in conjunction with pressure measurements or Doppler velocity (discussed in greater detail below). In some circumstances, it may be desired to perform a banding operation to obtain a specified vessel lumen radius r. In such cases, IVUS is well-suited to guide the banding operation as IVUS can directly reveal r. In fact, certain IVUS systems can instantly or automatically determine r upon an imaging operation and display r on a display such as that shown in FIG. 3.

Where it is desired to obtain a certain target vessel lumen radius r (e.g., 3 or 4 mm), method 101 involves determining that the target includes a 3 or 4 mm vessel lumen radius and using IVUS to evaluate the radius of the lumen of the fistula. The fistula is then banded. IVUS can be used to evaluate the parameter during banding, after banding, or both. IVUS can be used to determine that the banding operation has obtained the target, thus revealing that the banding procedure is complete.

In some embodiments, fistula banding is guided through the use of an instrumented guidewire that may include a pressure sensor, ultrasound transducer, or both.

Figure 4:
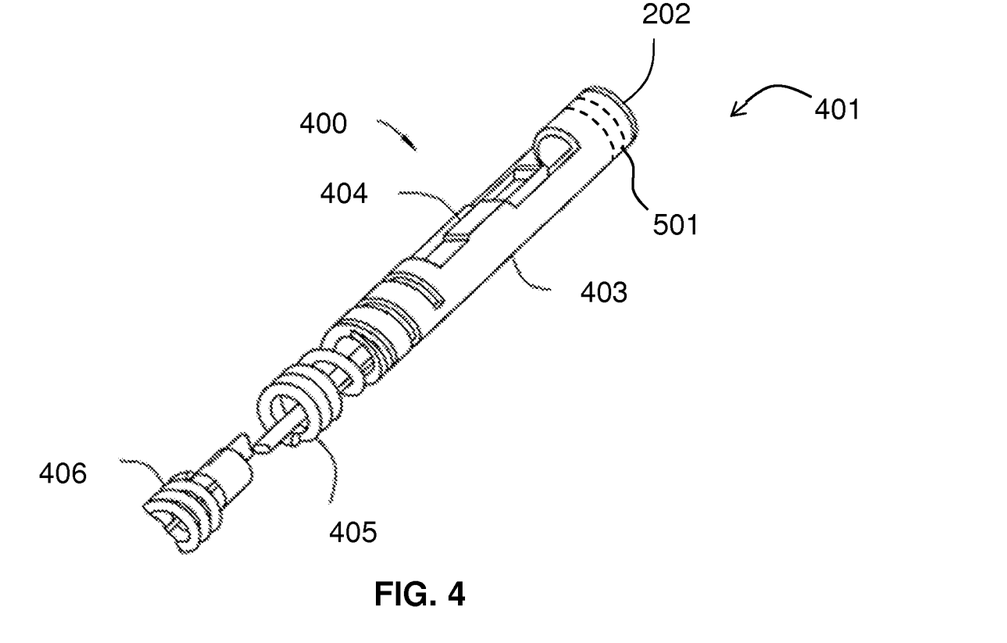
FIG. 4 shows a guidewire tip of embodiments of the invention.

FIG. 4 shows a sensor tip 400 of a guidewire 401 according to embodiments of the present invention. Guidewire 401 will include one of pressure sensor 404 and ultrasound transducer 501. In general, guidewire 401 will sensor housing 403 for pressure sensor 404, ultrasound transducer 501, or both and may optionally include a radiopaque tip coil 405 distal to proximal coil 406.

Pressure sensor 404 can detect a lack of a pressure gradient, indicating that the fistula is not restrictive enough (i.e., if blood flows through the fistula too freely, it will not also flow to distal extremities of that limb of the body, leading to distal ischemia). It may be found, for example, that a ΔP of less than 20 or 30 mmHg is problematic. Pressure sensors and their use are described in U.S. Pub. 2009/0088650 to Corl.

Ultrasound transducer 501 may include a forward-looking IVUS and can give the velocity of flow. Velocity data may be derived by the computer in the system from the Doppler frequency shifts detected in the ultrasound echo signals. Obtaining Doppler velocity is discussed in U.S. Pub. 2013/0303907 to Corl and U.S. Pub. 2007/0016034 to Donaldson.

Guidewire 401 may comprise a flexible elongate element having proximal and distal ends and a diameter of 0.018" or less as disclosed in U.S. Pat. No. 5,125,137, U.S. Pat. No. 5,163,445, U.S. Pat. No. 5,174,295, U.S. Pat. No. 5,178,159, U.S. Pat. No. 5,226,421, U.S. Pat. No. 5,240,437 and U.S. Pat. No. 6,106,476, all of which are incorporated by reference herein. Guidewire 401 can be formed of a suitable material such as stainless steel, Nitinol, polyimide, PEEK or other metallic or polymeric materials having an outside diameter for example of 0.018" or less and having a suitable wall thickness, such as, e.g., 0.001" to 0.002". This flexible elongate element is conventionally called a hypotube. In one embodiment, the hypotube may have a length of 130 to 170 cm. Typically, such a guide wire may further include a stainless steel core wire extending from the proximal extremity to the distal extremity of the flexible elongate element to provide the desired torsional properties to facilitate steering of the guide wire in the vessel and to provide strength to the guidewire and prevent kinking.

In a preferred embodiment, methods of the invention employ a guidewire with improved stiffness, relative to prior art guidewires. For example, the guidewire can include a stiffening material such as a stainless steel core or a less pliable plastic (e.g., less pliable than Nitinol, polyimide, or PEEK). Preferably, the guidewire has a flexural modulus of at least 15 GPa. In some embodiments, the guidewire has a flexural modulus of at least 50 GPa (e.g., as measured and described in Harrison et al., 2011, What's in a name?, J Endo Ther 18(6):797-801). For example, the guidewire may be made with the stiffness of an Amplatz type super-stiff or ultra-stiff guidewire. The guidewire can have a diameter of about 0.014" (0.35 mm) and can include the functional instrumentation of the Doppler guide wire sold under the name FLOWIRE by Volcano Corporation, the pressure guidewire sold under the name PRIMEWIRE PRESTIGE by Volcano Corporation, or both.

A pressure sensor allows one to obtain pressure measurements within a body lumen. A particular benefit of pressure sensors is that pressure sensors allow one to measure fractional flow reserve (FFR) in a vessel, which is a comparison of the pressure within a vessel at positions prior to, and after, a fistula. The level of FFR can indicate whether the fistula is a high-flow fistula, which allows a physician to accurate guide banding of a high flow fistula. For example, an FFR measurement significantly above 0.80 may indicate a high flow fistula. Another benefit is that a physician can measure the pressure before and after an intraluminal intervention procedure to determine the impact of the procedure.

Pressure sensor 404 can be mounted on the distal portion of a flexible elongate member. In certain embodiments, the pressure sensor is positioned distal to the compressible and bendable coil segment of the elongate member. This allows the pressure sensor to move away from the longitudinal axis and coil segment as bended. The pressure sensor can be formed of a crystal semiconductor material having a recess therein and forming a diaphragm bordered by a rim. A reinforcing member is bonded to the crystal and reinforces the rim of the crystal and has a cavity therein underlying the diaphragm and exposed to the diaphragm. A resistor having opposite ends is carried by the crystal and has a portion thereof overlying a portion of the diaphragm. Electrical conductor wires can be connected to opposite ends of the resistor and extend within the flexible elongate member to the proximal portion of the flexible elongate member. Additional details of suitable pressure sensors that may be used with devices of the invention are described in U.S. Pat. No. 6,106,476. U.S. Pat. No. 6,106,476 also describes suitable methods for mounting the pressure sensor 404 within a sensor housing. As discussed above, additionally or alternatively, a guidewire can include a flow sensor. In some embodiments, a guidewire is used that includes a flow sensor such as ultrasound transducer 501. A suitable product for guidewire 401 is the PrimeWire PRESTIGE from Volcano Corporation.

Ultrasound transducer 501 can provide a flow sensor that may be used to measure blood flow velocity within the vessel, which can be used to assess coronary flow reserve (CFR), or non-coronary vessel flow equivalent. The flow sensor can be, for example, an ultrasound transducer, a Doppler flow sensor or any other suitable flow sensor, disposed at or in close proximity to the distal tip of the guidewire. The ultrasound transducer may be any suitable transducer, and may be mounted in the distal end using any conventional method, including the manner described in U.S. Pat. Nos. 5,125,137, 6,551,250 and 5,873,835. A suitable product for guidewire 201 with a flow sensor 305 is the FLOWIRE from Volcano Corporation.

The ultrasound transducer 501 may be any suitable transducer, and may be mounted in the distal end using any conventional method, including the manner described in U.S. Pat. No. 5,125,137, which is fully incorporated herein by reference. Conductors (not shown) may be secured to the front and rear sides of the ultrasound transducer 501, and the conductors may extend interiorly to the proximal extremity of a guide wire.

The combination sensor tip 400 also includes a pressure sensor 404 also disposed at or in close proximity to the distal end of the combination sensor tip 400. The pressure sensor 404 may be of the type described in U.S. Pat. No. 6,106,476, which is fully incorporated herein by reference. For example, the pressure sensor 404 may be comprised of a crystal semiconductor material having a recess therein and forming a diaphragm bordered by a rim. A reinforcing member may be bonded to the crystal to reinforce the rim of the crystal, and may have a cavity therein underlying the diaphragm and exposed to the diaphragm. A resistor having opposite ends may be carried by the crystal and may have a portion thereof overlying a portion of the diaphragm. Leads may be connected to opposite ends of the resistor and extend proximally within the guide wire. Additional details of suitable pressure sensors that may be used as the pressure sensor 404 are described in U.S. Pat. No. 6,106,476. U.S. Pat. No. 6,106,476 also describes suitable methods for mounting the pressure sensor 404 within the combination sensor tip 400. In one embodiment, the pressure sensor 404 is oriented in a cantilevered position within a sensor housing 403. For example, the sensor housing 403 preferably includes a lumen surrounded by housing walls. When in a cantilevered position, the pressure sensor 404 projects into the lumen of the sensor housing 403 without contacting the walls of the sensor housing 403.

In FIG. 4, ultrasound transducer 501 is illustrated as disposed near the distal end of guidewire 401. One advantage of the sensor housing 403 is that because the sensor housing 403 encloses both the ultrasound transducer 501 and the pressure sensor 404, the need for two separate housings, i.e., one for an ultrasound transducer and one for a pressure sensor, is eliminated. Accordingly, the use of a common sensor housing 403 for the ultrasound transducer 501 and the pressure sensor 404 makes the combination sensor tip 400 easier to manufacture than current designs.

Additionally, unlike prior art designs, the combination sensor tip 400 of the present invention provides for both the ultrasound transducer 501 and the pressure sensor 404 to be disposed near the distal end of the combination sensor tip 400. The combination sensor tip 400 of the present invention is advantageous over prior art designs because by having both the ultrasound transducer 501 and the pressure sensor 404 near its distal end, the combination sensor tip 400 is capable of being positioned further distally in a vessel or the body than the prior art designs. Additionally, the combination sensor tip 400 of the present invention, unlike the prior art, is also able to take measurements from the ultrasound transducer 501 and the pressure 104 at approximately the same location and approximately the same time, thereby resulting in greater consistency of measurements, greater accuracy of measurements, and greater accuracy of placement within the body. Furthermore, placement of both the ultrasound transducer 501 and the pressure sensor 404 near the distal end of the combination sensor tip 400 increases overall flexibility in a guide wire that incorporates the combination sensor tip 400. For example, a prior art guide wire that includes separate sensors, with the pressure sensor being located substantially proximal from the ultrasound transducer, has a longer relatively rigid area that must be devoted to the pressure and flow sensors, i.e., the distance from the ultrasound transducer to the pressure sensor. The present invention, in contrast, substantially reduces or entirely eliminates the distance between the ultrasound transducer and the pressure sensor, thereby allowing for increased flexibility across this length.

It should be noted that in an alternative embodiment of the combination sensor tip 400 (not shown) both the ultrasound transducer 501 and the pressure sensor 404 may be offset from the distal end of the combination sensor tip 400, such as, e.g., 1.5 cm to 3.0 cm from the distal end, but still located in close proximity to each other relative to prior art designs. Thus, the aforementioned advantages over the prior art design are still achieved.

In an alternative embodiment, the pressure sensor housing includes a tubular member having an opening on the outer wall in communication with the lumen and a tip. The tip is constructed of a solder ball. Alternatively a weld, braze, epoxy or adhesive can be used. The lumen of the housing is counter-bored so that the lumen has a smaller inner diameter at the proximal end of the tubular member. For example, the housing may be constructed in the counter-bore fashion with a 0.010" inner diameter at the proximal end and a 0.012" inner diameter at the distal end, with the pressure transducer coaxially housed in the lumen. In addition, a flow sensor may be placed in the sensor tip instead of the weld, braze, epoxy or adhesive to provide a combo sensor tip. The advantage of the counter bore is that the housing is easier to make. The transducer is simply slid into place in the lumen and bonded (adhesive or epoxy) where the sides meet the proximal 0.010" inner diameter 314. The distal 0.012" inner diameter allows enough room for the pressure sensitive section of the transducer to be free from any contact with the housing. Because of the counter-bored lumen, there is no ledge that has to be made on the outer wall of the lumen, rather the pressure transducer communicates with the outside via an opening in the outer wall of lumen. Constructions suitable for use with a guidewire of the invention are discussed in U.S. Pub. 2013/0030303 to Ahmed, the contents of which are incorporated by reference.

A radiopaque tip coil 405 may be provided at the proximal end of the combination sensor tip 400. The radiopaque tip coil 405 is coupled to a proximal coil 106, and the proximal coil 106 may be coupled to the elongate tubular member. The depicted embodiment provides a smooth transition from the elongate tubular member to the combination sensor tip 400, i.e., the connection between the radiopaque tip coil 405, the proximal coil 106, and the rest of the guide wire is optimized relative to current designs. Specifically, the transition is smoother and more flexible because of the absence of the housing between the radiopaque tip coil 405 and the proximal coil 106. Current designs generally have a tip coil 5 attached to a pressure sensor housing 3, which in turn is connected to a proximal coil 6. The present invention eliminates or greatly reduces the separation between the tip coil and the proximal coil that is required in current devices. Suitable coils for use with the present invention are described in U.S. Pat. No. 6,106,476.

Preferably, guidewire 401 includes conductors passing through the guide wire to conductive bands near the proximal end of the guide wire. Signals from the ultrasound transducer 501 and the pressure sensor 404 may be carried by the conductors. Usually three electrical connectors are necessary for a stand-alone pressure measurement guidewire and two electrical connectors are necessary for a stand-alone flow measurement guidewire. Thus, a guide wire incorporating the combination sensor tip 400 of the present invention includes five electrical conductors extending through the guidewire. The conductive bands may be electrically isolated from each other by means of epoxy or polyimide.

The electrical connection wires can include a conductive core made from a conductive material, such as copper, and an insulating coating, such as a polyimide, Fluoro-polymer, or other insulating material. The electrical connection wires extend from one or more sensors located on the distal end of the guidewire, run down the length of the guidewire, and connect to a connector housing at a proximal end.

Any suitable arrangement of the electrical connection wires through the length of the elongate member can be used. The arrangement of electrical connection wires must provide for a stable connection from the proximal end of the guidewire to the distal end of the guidewires. In addition, the electrical connection wires must be flexible and/or have enough slack to bend and/or move with the adjustable distal portion without disrupting the sensor connection. In one embodiment, the electrical connections run next the core member within the lumen of the elongate member.

In yet another embodiment, the electrical connector wires are wrapped around a core member of the guidewire and then covered with a polyimide layer. At a distal end of the core member near the sensors, the polyimide layer can be dissected away, which frees the wires to extend and connect to their respective sensors. The length of the electrical connector wire running free from the core member and connected to the sensor should have enough slack/flexibility to remain connected to the sensor during bending of the guidewire.

Preferably, a proximal end of guidewire 401 connects to connector housing 215 similar to that shown in FIG. 2. In certain embodiments, the electrical connector wires are joined together to form a male connector at a proximal end. The male connector mates with a female connector of the connector housing. The termination of the male connector can be performed by a metal deposition process as described in U.S. Pat. No. 6,210,339, incorporated herein by reference in its entirety. The deposited metal (or any conductive material) permanently adheres or couples to the exposed conductive wires at points where the polyimide layers were removed. After the masking material is removed, there are independent conductive stripes, each connected to a different respective electric wire. Because of the precision nature of the winding process as well as the masking and metal deposition processes, a male connector is made that is short in length, yet very reliable, in mating with a female connector and cable. Alternatively, conductive bands may be coupled to the exposed ends of the electric wires instead of the metallizing process.

The connector housing can be connected to an instrument, such as a computing device (e.g. a laptop, desktop, or tablet computer) or a physiology monitor, that converts the signals received by the sensors into pressure and velocity readings in systems of the invention.

The connector housing can be connected to an instrument, such as a computing device (e.g. a laptop, desktop, or tablet computer) or a physiology monitor, that converts the signals received by the sensors into pressure and velocity readings in systems of the invention.

Figure 5:
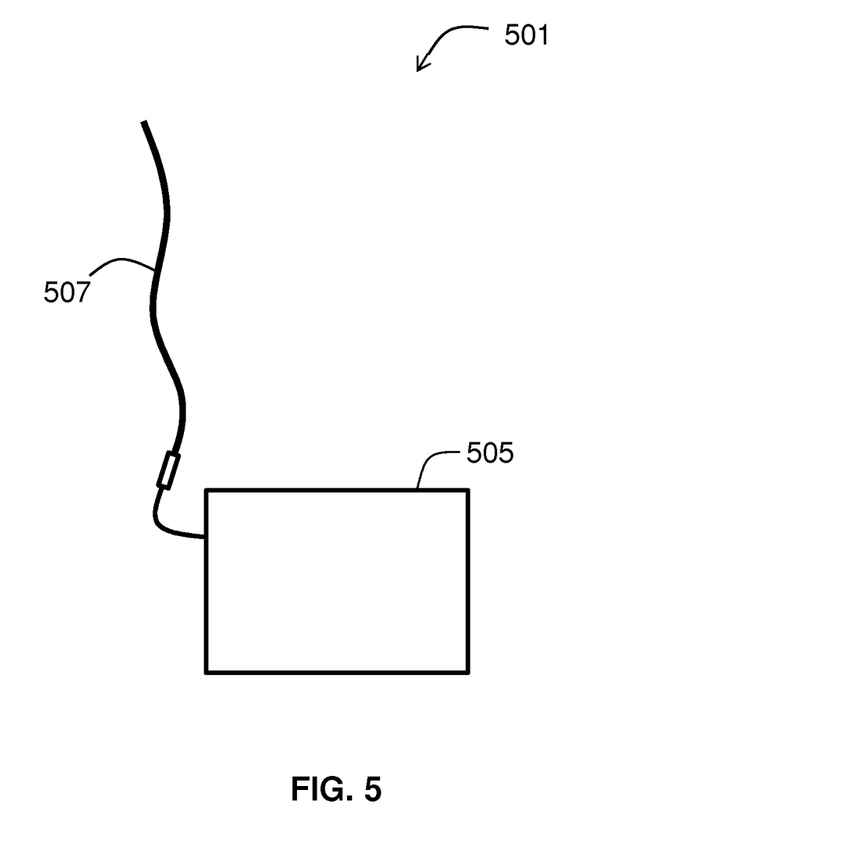
FIG. 5 diagrams a system of the invention.

FIG. 5 illustrates a system 501 of the invention. System 501 includes an intravascular instrument 507 operably coupled to a computer device 505. Intravascular instrument 507 includes at least one sensor such as an IVUS imaging device, a pressure sensor, or a flow sensor as discussed above. Intravascular instrument 507 may include a plurality of sensors such as a pressure sensor and a flow sensor as discussed above. Computer 505 can be a dedicated medical imaging instrument, a standard desktop, laptop, or tablet computer, or a combination thereof (e.g., a medical imaging instrument with a base station and a laptop or desktop computer attached to provide a workstation and interface for a physician.

Computer 505 can receive a measurement from the sensor on intravascular instrument 507 and use the measurement to determine a need for restriction of flow through a fistula. In some embodiments, computer 505 compares an observed measure, such as patency (indicated by radius) or flow rate (e.g., from Doppler flow) to a standard or expected measure to provide an aid in guiding banding.

For example, computer 505 may have a software program in memory that stores a standard (e.g., <8 mm diameter patency or <800 mL/min flow rate). By making a comparison, if the measured value does not meet the standard, the physician can determine to band or further restrict the fistula. If or when the measured value meets the standard, the fistula is deemed to need no further restriction. The instrument can further calculate Coronary Flow Reserve (CFR)—or similar—and Fractional Flow Reserve (FFR) and provide the readings and calculations for any of the measurements to a user via a user interface.

In some embodiments, a user interacts with a visual interface to view images from the imaging system. Input from a user (e.g., parameters or a selection) are received by a computer device or processing instrument. Electrical signals are relayed from the conductors via a mating connector (or contact housing as described herein with respect to a connector of the present invention) to an instrument, such as, e.g., a physiology monitor, that converts the signals into pressure and velocity readings that are displayed to the user. In addition algorithms such as Coronary Flow Reserve (CFR) (or similar) and Fractional Flow Reserve (FFR) are calculated.

System 501 may include one or a plurality of computer. For example, system 501 may include computer 505 as a bed-side workstation or in a control room and system 501 may additionally include a server computer for processing measurements or for receiving measurements from a plurality of cath labs. A computer in system 501 such as computer 505 generally includes a processor coupled to memory and one or more input/output devices. Computer 505 may be provided by a desktop computer, laptop, tablet, mobile device, or purpose-built machine (such as a bed-side control station for a medical imaging system).

A processor generally refers to a computer microchip such as the processor sold under the trademark CORE 17 by Intel (Santa Clara, Calif.).

Memory generally includes one or more devices for random access, storage, or both. Preferably, memory includes a tangible, non-transitory computer readable medium, and may be provided by one or more of a solid state drive (SSD), a magnetic disc drive (aka, "a hard drive"), flash memory, an optical drive, others, or a combination thereof.

An I/O device may include one or more of a monitor, keyboard, mouse, touchscreen, Wi-Fi card, cell antenna, Ethernet port, USB port, light, accelerometer, speaker, microphone, drive for removable disc, others, or a combination thereof. Preferably, any combination of computer in system 501 may communicate through the use of a network, which may include communication devices for internet communication, telephonic communication, others, or a combination thereof.

Intravascular instrument 507 (e.g., as used with system 501) can reveal, through IVUS, pressure measurements, or Doppler velocity, flow through the fistula, patency, or both. In some circumstances, it may be desired to perform a banding operation to obtain a specified patency or vessel volume flow. In such cases, intravascular instrument 507 is well-suited to guide the banding operation as intravascular instrument 507 can directly reveal patency or flow. In fact, certain intravascular instrument systems can instantly or automatically determine flow upon measuring operation and display flow on a display on computer 505.

In advanced embodiments, the systems of the invention incorporate focused acoustic computed tomography (FACT), which is described in WO2014/109879, incorporated herein by reference in its entirety.

Where it is desired to obtain a certain target patency (e.g., less than 8 mm diameter), method 101 involves establishing the target to be diameter=8 mm (e.g., within computer 505) and using an IVUS catheter 201 to evaluate the patency of the fistula. The fistula is then banded. Cather 201 can be used to evaluate the diameter during banding, after banding, or both. Catheter 201 can be used to determine that the banding operation has obtained the target diameter, thus revealing that the banding procedure is complete.

Where it is desired to obtain a certain target vessel flow (e.g., less than 0.8 L/min), method 101 involves establishing the target to be flow rate=0.8 L/min (e.g., within computer 505) and using an instrumented guidewire 401 to evaluate the flow rate within the fistula. The fistula is then banded. Guidewire 401 can be used to evaluate the flow parameter during banding, after banding, or both. Guidewire 401 can be used to determine that the banding operation has obtained the target flow rate, thus revealing that the banding procedure is complete.

Banding generally refers to procedures for restricting flow through a fistula.

The introduction of a high-resistance band is a reasonable treatment for a low-resistance venous pathway, which has transformed a functional access into a pathologic shunt. Banding physiology is best explained by Poiseuille's law, which states that for laminar flow, volume flow rate Q is given by pressure drop across a gradient ($\Delta P$) (e.g., arterial pressure-central venous pressure) divided by the viscous resistance R, where R is given by $8 \mu L/\pi r4$, with $\mu$ being the fluid viscosity and r is the radius of the vessel. Thus, Q is $\Delta P \pi r4/8 \mu L$.

Banding techniques decrease flow by decreasing the radius at a specific point, and as a result, access flow and pressure are directly sacrificed to increase distal arterial flow and pressure. Any suitable banding technique can be used.

Figure 6:
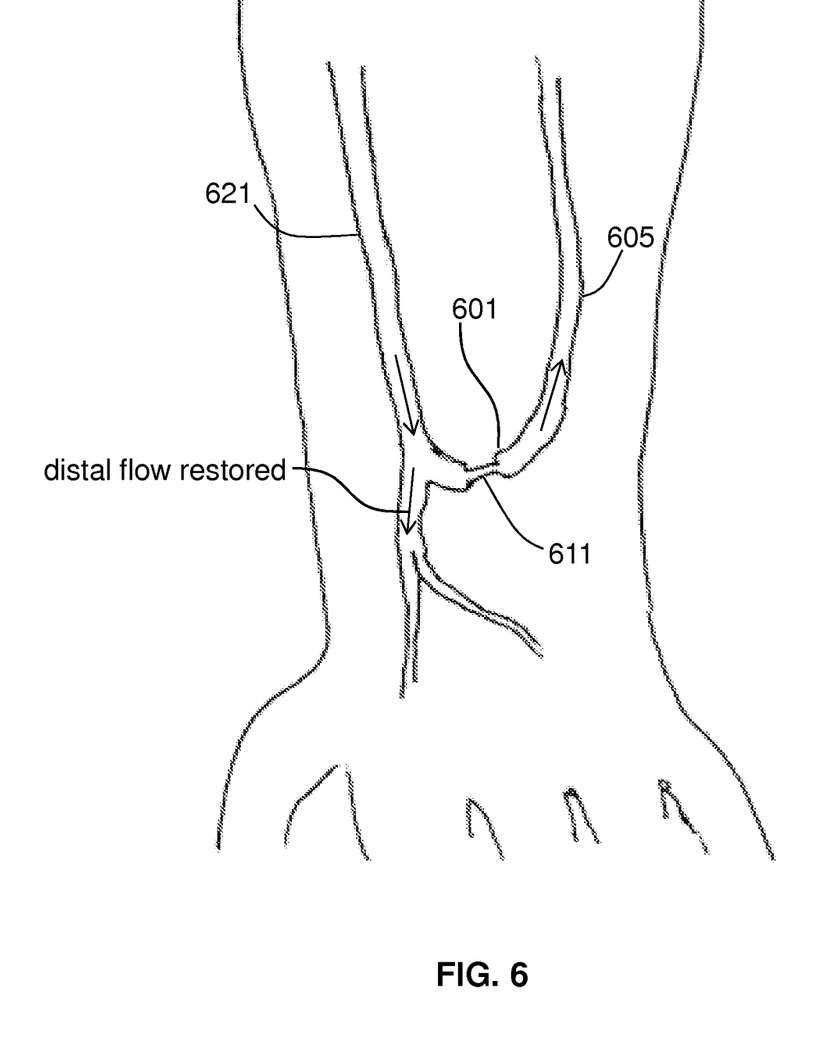
FIG. 6 illustrates a flow result obtained by banding a fistula or graft.

FIG. 6 illustrates a flow result obtained by banding a fistula. As shown in FIG. 6, blood flows into an arm from artery 621 and through fistula 601 to vein 605. Banding is performed at site 611 and the band 611 restores flow to distal parts of the limb. Exemplary banding techniques include, for example, use of a narrowing suture, plication, minimally invasive limited ligation endoluminal-assisted revision (MILLER) banding, tapering, and surgical banding. See, e.g., West, et al., 1991, Arterial insufficiency in hemodialysis access procedures: correction by banding technique, Transpl Proc 23 (2): 1838-40; Rivers, et al., 1992, Correction of steal syndrome secondary to hemodialysis access fistulas: a simplified quantitative technique, Surgery 112(3):593-7; Kirkman, 1991, Technique for flow reduction in dialysis access fistulas, Surg Gyn Obstet 172(3):231-3; and Mickley, 2008, Steal Syndrome—strategies to preserve vascular access and extremity, Nephrol Dial Transplant 23:19-24.

One favored approach to banding is the MILLER technique. In this procedure, the fistula is exposed and a 4-5 mm balloon is introduced into the fistula and inflated. A non-resorbable suture is tied around the inflated balloon and vein to achieve a defined reduction in balloon diameter.

The MILLER banding technique overcomes the inherent difficulties of sizing associated with banding by using a 3- or 4-mm diameter intraluminal balloon as a sizing dowel. Once the subcutaneous 2-0 prolene suture is tied around the outside of the vessel, the intraluminal balloon ensures that the end lumen diameter is precise and predictable. Bands that are too tight can be stretched or even broken using an angioplasty technique. If a band is too loose, the procedure is easily repeated because it is minimally invasive. It can be safely performed in an outpatient setting with good outcomes and minimal associated morbidity. See Miller, et al., 2009, The MILLER banding procedure is an effective method for treating dialysis-associated steal syndrome, Kidney Int 1-8; and Miller et al., 2006, Minimally Invasive Limited Ligation Endoluminal-assisted Revision (MILLER) for treatment of dialysis access-associated steal syndrome, Kidney Int 70(4):765-70.

Another useful approach to surgical banding is described as T-banding. For T-banding, an expanded polytetrafluoroethylene (PTFE) graft is used. Preferably, the graft has length of about 60 mm and a diameter of about 8 mm. The graft is cut along its length to create a 60 mm×24 mm patch. The diameter of arterial inflow and outflow in the patient is measured and the patch is cut into a cross-shape that folds into a T-shaped junction characterized by the arterial inflow and outflow diameters on the opposed short ends of the T, with the long end of the T having a diameter of about 6 mm. This patch is then positioned in situ and closed with a running suture on both sides, forming a T-band. While suturing, arterial inflow is clamped to reduce the pressure. T-banding is described in Schneider, et al., 2006, T-banding: A technique for flow reduction of a hyper-functioning arteriovenous fistula, J Vasc Surg. Surgical banding is also discussed in Anderson and Groce, 1975, Banding of arteriovenous dialysis fistulas to correct high-output cardiac failure, Surgery 78(5):552-4. Whatever banding technique is employed, a result may include the restoration of flow to distal extremities, to remedy distal ischemia, as well as relief of cardiac overload associated with high-flow fistula. Thus, as discussed above, the invention relates to restricting flow through arteriovenous (AV) fistula using intravascular measurements to guide the procedure. The invention provides systems and methods for using intravascular detection to guide the restriction of flow through a vascular access site. A vascular access site includes arteriovenous (AV) fistulas and grafts. An AV fistula is a surgically-created or induced native channel formed to connect an artery to a vein, whereas an AV graft is an artificial connection (such as a synthetic material) that connects the artery to the vein. "AV access site" or "hemodialysis AV shunt" are alternate ways of describing both fistulas and grafts. An intravascular instrument such as an imaging catheter or guidewire with measuring capabilities is inserted into a vessel proximal to a vascular access site and used to evaluate the site, which is banded to obtain healthy flow as indicated by the intravascular instrument. In certain aspects, the invention provides a method for improving a hemodialysis fistula by inserting an intravascular instrument into a vessel proximal to the fistula, making a measurement with the intravascular instrument, and restricting flow through the fistula until the measurement obtains a predetermined value.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

The invention claimed is:

1. A method for improving a hemodialysis vascular access site, the method comprising:
   providing an intravascular instrument comprising an elongate tubular member, a proximal coil coupled to the elongate tubular member, a tip coil and a combination sensor tip having a housing, the tip coil and the proximal coil being different coils, wherein the housing comprises a proximal end coupled to the tip coil, wherein the combination sensor tip comprises a pressure sensor and an intravascular ultrasound (IVUS) transducer configured to acquire cross-sectional views, wherein the pressure sensor and the IVUS transducer are disposed within the housing;
   inserting the intravascular instrument into a vessel proximal to the hemodialysis vascular access site with guidance from imaging provided by the IVUS transducer in the combination sensor tip at the distal end of the intravascular instrument;
   making a measurement with the pressure sensor at the distal end of the intravascular instrument; and
   restricting flow through the hemodialysis vascular access site by banding while directly monitoring a radius or diameter of the vascular access site undergoing the banding using cross-sectional views acquired by the IVUS transducer until the radius or diameter of the vascular access site determined by the direct monitoring obtains a predetermined value.

2. The method of claim 1, wherein the intravascular instrument is an instrumented guidewire.

3. The method of claim 1, wherein the IVUS is further configured to acquire views along a vessel axis, and the inserting of the intravascular instrument into the vessel is with guidance from views along the vessel axis provided by the IVUS transducer.

4. The method of claim 1, wherein the measurement comprises a rate of flow through the vascular access site and the vascular access site is one selected from the list consisting of an arteriovenus fistula and a graft.

5. The method of claim 1, wherein the tip coil has at least one distinguishing characteristic from the proximal coil.

6. The method of claim 5, wherein the at least one distinguishing characteristic is the tip coil is radiopaque.

7. The method of claim 1, wherein the pressure sensor is disposed proximally of the IVUS transducer within the housing.

8. A system for vascular access site banding, the system comprising:
an intravascular instrument dimensioned to be inserted into a vessel proximal to the vascular access site and operable to measure a property therein, the intravascular instrument comprising an elongate tubular member, a proximal coil coupled to the elongate tubular member, a tip coil coupled to the proximal coil, the tip coil and the proximal coil being different coils, and a combination sensor tip, wherein the combination sensor tip comprises a housing, a pressure sensor and an IVUS transducer configured to acquire both cross-sectional views and views along a vessel axis, wherein the pressure sensor and the IVUS transducer are disposed within the housing, wherein the housing comprises a proximal end coupled to the tip coil; and
a computer coupled to the intravascular instrument and operable to:
receive the measured property from the combination tip of the intravascular instrument and to evaluate a need for restriction of blood flow through the arteriovenous vascular access site based upon the measured property;
monitor banding of the arteriovenous vascular access site by acquiring cross-sectional views using the IVUS and display a radius or diameter of the arteriovenous vascular access site determined from the cross-sectional views during the banding.

9. The system of claim 8, wherein the intravascular instrument is an instrumented guidewire.

10. The system of claim 8, wherein the computer is operable to evaluate whether the measured property obtains a predetermined value and to guide a decision about further restriction of flow based upon whether the measured property obtains the predetermined value.

11. The system of claim 10, wherein the measured property comprises a rate of flow through the vascular access site.

12. The system of claim 11, wherein the predetermined value is less than 800 mL/min.

13. The system of claim 10, wherein the measured property comprises a radius or diameter of the vascular access site.

14. The system of claim 13, wherein the predetermined diameter value is less than 8 mm.

15. The system of claim 8 wherein
the IVUS transducer is further configured to measure Doppler flow velocity;
the measured property further comprises a flow velocity measured using the IVUS; and
the computer is further operable to compute a flow volume based on the flow velocity and further based on the radius or diameter.

16. The system of claim 8 wherein the measured property is a pressure measurement by the pressure sensor that describes a pressure gradient of the arteriovascular access site.

17. The system of claim 8, wherein the tip coil has at least one distinguishing characteristic from the proximal coil.

18. The system of claim 17, wherein the at least one distinguishing characteristic is the tip coil is radiopaque.

* * * * *